(12) United States Patent
Han et al.

(10) Patent No.: US 10,585,509 B2
(45) Date of Patent: Mar. 10, 2020

(54) DISPLAY SUBSTRATE AND DISPLAY APPARATUS

(71) Applicant: BOE TECHNOLOGY GROUP CO., LTD., Beijing (CN)

(72) Inventors: Yanling Han, Beijing (CN); Xue Dong, Beijing (CN); Jing Lv, Beijing (CN); Haisheng Wang, Beijing (CN); Chunwei Wu, Beijing (CN); Xiaoliang Ding, Beijing (CN); Wei Liu, Beijing (CN); Pengpeng Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/762,538

(22) PCT Filed: Jun. 29, 2017

(86) PCT No.: PCT/CN2017/090689
§ 371 (c)(1),
(2) Date: Mar. 22, 2018

(87) PCT Pub. No.: WO2018/028328
PCT Pub. Date: Feb. 15, 2018

(65) Prior Publication Data
US 2019/0079616 A1    Mar. 14, 2019

(30) Foreign Application Priority Data

Aug. 12, 2016  (CN) .......................... 2016 1 0663489

(51) Int. Cl.
*G06F 3/041* (2006.01)
*G06F 3/044* (2006.01)
(Continued)

(52) U.S. Cl.
CPC ........ *G06F 3/0412* (2013.01); *A61B 5/14539* (2013.01); *A61B 5/6897* (2013.01);
(Continued)

(58) Field of Classification Search
CPC ...... G06F 3/0412; G06F 3/0416; G06F 3/044; G06F 3/041; G02F 1/13338; G05D 21/02; H01L 27/323; A61B 5/00
See application file for complete search history.

(56) References Cited

U.S. PATENT DOCUMENTS

2011/0025602 A1* 2/2011 Sivan ................... G09B 21/003
    345/156
2015/0331518 A1* 11/2015 Kaneko ................. G06F 3/0412
    345/174
(Continued)

FOREIGN PATENT DOCUMENTS

CN    104808867 A    7/2015
CN    104883970 A    9/2015
(Continued)

OTHER PUBLICATIONS

Office Action received for Chinese Patent Application No. 201610663489.X, dated May 16, 2017, 15 pages (8 pages of English Translation and 7 pages of Office Action).
(Continued)

*Primary Examiner* — Amit Chatly
(74) *Attorney, Agent, or Firm* — Womble Bond Dickinson (US) LLP (57) ABSTRACT

This document describes a display substrate and a display apparatus. The display substrate comprises a base, a plurality of drive signal lines, a plurality of pH value detection signal lines, and a plurality of pH value sensing modules arranged on the base; each pH value sensing module is connected to a corresponding drive signal line and a corre-
(Continued)

sponding pH value detection signal line; the drive signal line is configured to provide a drive signal to the pH value sensing modules connected thereto so as to control said pH value sensing modules to work or not; the pH value sensing module is configured to sense a pH value under a working state and output a corresponding electrical signal; the pH value detection signal line is configured to receive the electrical signal output by the pH value sensing module.

19 Claims, 4 Drawing Sheets

(51) Int. Cl.
*A61B 5/00* (2006.01)
*A61B 5/145* (2006.01)
*G02F 1/1333* (2006.01)
*G05D 21/02* (2006.01)
*H01L 27/32* (2006.01)

(52) U.S. Cl.
CPC ......... *G02F 1/13338* (2013.01); *G05D 21/02* (2013.01); *G06F 3/044* (2013.01); *G06F 3/0416* (2013.01); *H01L 27/323* (2013.01)

(56) References Cited

U.S. PATENT DOCUMENTS

2017/0010238 A1* 1/2017 Johnson ............. G01N 27/4167
2017/0097734 A1 4/2017 Yang et al.

FOREIGN PATENT DOCUMENTS

| CN | 105510388 A | 4/2016 |
| CN | 205263683 U | 5/2016 |
| CN | 106293234 A | 1/2017 |

OTHER PUBLICATIONS

Office Action received for Chinese Patent Application No. 201610663489.X, dated Aug. 31, 2017, 8 pages (5 pages of English Translation and 3 pages of Office Action).
International Search Report received for PCT Patent Application No. PCT/CN2017/090689, dated Sep. 28, 2017, 5 pages (2 pages of English Translation and 3 pages of Original Document).
Decision on Rejection received for Chinese Patent Application No. 201610663489.X, dated Jan. 31, 2018, 10 pages (7 pages of English Translation and 3 pages of Office Action).
Written Opinion received for PCT Patent Application No. PCT/CN2017/090689, dated Sep. 28, 2017, 4 pages of Original Document Only.
Chinese Search Report received for Chinese Patent Application No. 201610663489.X, dated Feb. 16, 2017, 16 pages (8 pages of English Translation and 8 pages of Office Action).

\* cited by examiner

DISPLAY SUBSTRATE AND DISPLAY APPARATUS

RELATED APPLICATION

The present application is the U.S. national phase entry of PCT/CN2017/090689, with an international filing date of Jun. 29, 2017, which claims the benefit of Chinese Patent Application No. 201610663489.X filed on Aug. 12, 2016, the entire disclosures of which are incorporated herein by reference.

TECHNICAL FIELD

The present disclosure relates to the technical field of display, in particular to a display substrate and a display apparatus.

BACKGROUND

Modern people are usually under a sub-health condition for a long time because of the great life pressure, the unhealthy eating habits, etc., and if this condition continues, various diseases will be caused to seriously endanger people's health. Normally, people should be in an alkaline physical condition, and if a change towards a weak acid condition can be detected in time and can be intervened by a change of diet, etc., keeping healthy would not be so hard.

At present, display devices like mobile phone terminals are widely used, and if a pH value sensing circuit can be combined with the display devices, especially with mobile phone terminals, the pH values of holders of the terminals can be sensed in real time so as to determine the physical condition of the body.

SUMMARY

According to an aspect of the present disclosure, a display substrate is provided, which comprises: a base, a plurality of drive signal lines, a plurality of pH value detection signal lines, and a plurality of pH value sensing circuits arranged on the base; each of said plurality of pH value sensing circuits being connected to a corresponding drive signal line and a corresponding pH value detection signal line; wherein the drive signal line is configured to provide a drive signal to the pH value sensing circuits connected thereto so as to control said pH value sensing circuits to work or not;

the pH value sensing circuit is configured to sense a pH value under a working state and output a corresponding electrical signal;

the pH value detection signal line is configured to receive the electrical signal output by the pH value sensing circuit.

Optionally, orthographic projections of said plurality of drive signal lines and said plurality of pH value detection signal lines are crossing, and a pH value sensing circuit is arranged within an area defined by each crossing position.

Further optionally, each of the pH value sensing circuits comprises a pH value sensing transistor and a pH value sensing electrode, a first terminal of said pH value sensing transistor is connected to a first terminal of the pH value sensing electrode, and a second terminal of the pH value sensing electrode is connected to a fixed power supply terminal; and wherein, control terminals of the pH value sensing transistors in the same row are connected to the same drive signal line; and second terminals of the pH value sensing transistors in the same column are connected to the same pH value detection signal line.

Further optionally, said pH value sensing transistor is a double-gate thin film transistor.

Optionally, said display substrate further comprises a plurality of touch signal lines and a plurality of sensing signal lines arranged on the base; wherein said plurality of touch signal lines and said plurality of sensing signal lines have crossing orthographic projections on the base to define a plurality of touch areas; a fingerprint identification circuit is arranged in each of said plurality of touch areas; said fingerprint identification circuit is connected to a corresponding touch signal line and a corresponding sensing signal line and is configured to identify fingerprints. Further optionally, at least some of said plurality of touch areas have the pH value sensing circuits arranged therein.

Further optionally, said touch signal lines and said drive signal lines are arranged in the same layer and are of the same material.

Further optionally, said sensing signals lines and said pH value detection signal lines are arranged in the same layer and are of the same material.

Further optionally, in a pH value detection phase, said touch signal lines are multiplexed as said drive signal lines so as to provide drive signals to said pH value sensing circuits.

Alternatively, in the pH value detection phase, said sensing signal lines are multiplexed as said pH value detection signal lines so as to receive electrical signals output from said pH value sensing circuits.

Further optionally, each of the fingerprint identification circuits comprises a touch transistor and a photosensitive device, a first terminal of said touch transistor is connected to a first terminal of said photosensitive device, and a second terminal of said photosensitive device is connected to the fixed power supply terminal; and wherein control terminals of the touch transistors in the same row are connected to the same touch signal line; and second terminals of the touch transistors in the same column are connected to the same sensing signal line.

Optionally, said display substrate further comprises a plurality of touch electrodes and a plurality of sensing electrodes arranged on the base, and wherein orthographic projections of said plurality of touch electrodes and said plurality of sensing electrodes on the base are crossing.

Further optionally, said plurality of touch electrodes and said plurality of sensing electrodes have crossing orthographic projections on the base to define a plurality of touch areas; wherein at least some of said plurality of touch areas have the pH value sensing circuits arranged therein.

Further optionally, in the pH value detection phase, said touch electrodes are multiplexed as the drive signal lines so as to provide drive signals to said pH value sensing circuits.

Alternatively, in the pH value detection phase, said sensing electrodes are multiplexed as the pH value detection signal lines so as to receive electrical signals output from the pH value sensing circuits.

Optionally, said display substrate further comprises a signal processing circuit, which is connected to the pH value detection signal lines and is configured to receive and process the electrical signals read in said pH value detection signal lines so as to obtain pH values corresponding to said electrical signals.

According to a second aspect of the present disclosure, a display apparatus is further provided, which comprises any one of the above-mentioned display substrates.

DETAILED DESCRIPTION

The reference signs are listed as follows:
1: drive signal line; 2: pH value detection signal line; 3: pH value sensing circuit; 4: touch signal line; 5: sensing signal line; 6: fingerprint identification circuit; 7: touch electrode; 8: sensing electrode; T1: pH value sensing transistor; T2: touch transistor; 31: pH sensing electrode; 61: photosensitive device.

In order to enable those skilled in the art to better understand the technical solutions of the present disclosure, the present disclosure will be described in further detail below in conjunction with the drawings and the specific embodiments.

First Embodiment

Figure 1:
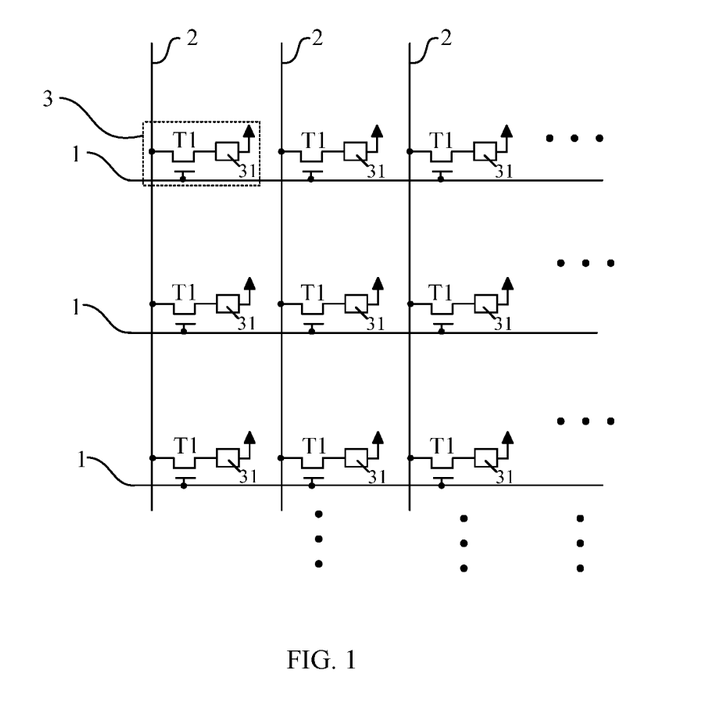
FIG. 1 is a structural diagram of a display substrate according to a first embodiment of the present disclosure.
Figure 2:
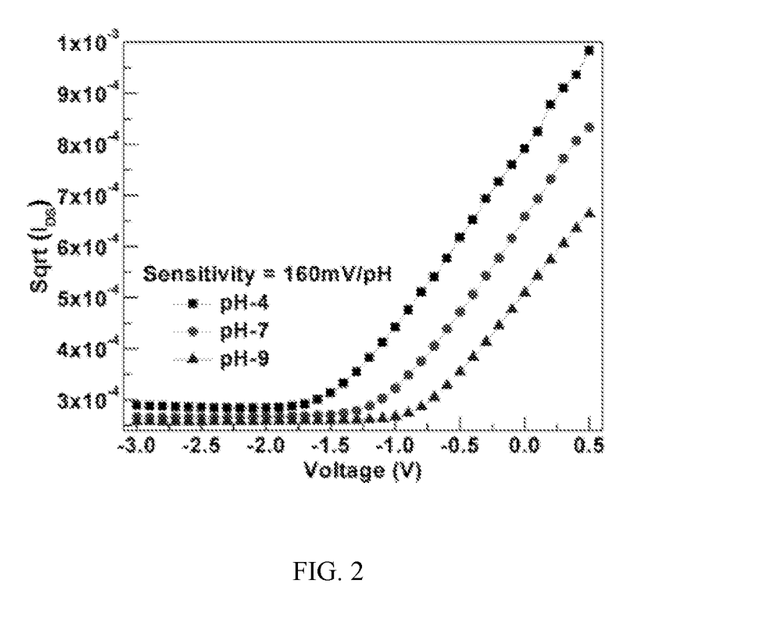
FIG. 2 is a schematic drawing of a relationship between a threshold voltage of a double-gate thin film transistor and a pH value accuracy in the display substrate according to the first embodiment of the present disclosure.

As shown in FIGS. 1 and 2, this embodiment provides a display substrate, which comprises: a base, a plurality of drive signal lines 1, a plurality of pH value detection signal lines 2, and a plurality of pH value sensing circuits 3 arranged on the base; each of said plurality of pH value sensing circuits 3 being connected to a corresponding drive signal line 1 and a corresponding pH value detection signal line 2; wherein the drive signal line 1 is configured to provide a drive signal to the pH value sensing circuits 3 connected thereto so as to control said pH value sensing circuits 3 to work or not; the pH value sensing circuit 3 is configured to sense a pH value under a working state and output a corresponding electrical signal; the pH value detection signal line 2 is configured to receive the electrical signal output by the pH value sensing circuit 3. Said electrical signal can be used for determining pH value of a user.

Of course, the display substrate in this embodiment may further comprise a signal processing circuit, which is connected to the pH value detection signal lines 2 and is configured to receive and process the electrical signals received on said pH value detection signal lines 2 so as to obtain pH values corresponding to the electrical signals.

The display substrate in this embodiment comprises the pH value sensing circuit 3 for sensing pH values of human bodies, and said pH value sensing circuit 3 works when the drive signal line 1 connected with it supply a drive signal. If a user touches the display substrate at the position of the pH value sensing circuit 3, then said pH value sensing circuit 3 will be able to sense a pH value of said user and output a corresponding electrical signal to the pH value signal line, so that the signal processing circuit can analyze the pH value of said user through the electrical signal, thereby determining the health condition of said user.

Specifically, as shown in FIG. 1, in this embodiment, the plurality of drive signal lines 1 and the plurality of pH value detection signal lines 2 in the display substrate have crossing orthographic projections on the base; and a pH value sensing circuit 3 is arranged within an area defined by each crossing position. It can be seen that the plurality of pH value sensing circuits 3 in the display substrate in this embodiment are arranged as a matrix, such that the plurality of pH value sensing circuits 3 are uniformly distributed in the display substrate, which will result in uniform display of the display substrate and more accurate detection of the pH value of the user. Of course, the pH value sensing circuits 3 may be arranged only in areas defined by some of the crossing positions.

Each of the pH value sensing circuits 3 comprises a pH value sensing transistor T1 and a pH value sensing electrode 31, a first terminal of said pH value sensing transistor T1 is connected to a first terminal of the pH value sensing electrode 31, and a second terminal of the pH value sensing electrode 31 is connected to a fixed power supply terminal; and wherein control terminals of the pH value sensing transistors T1 in the same row are connected to the same drive signal line 1; and second terminals of the pH value sensing transistors T1 in the same column are connected to the same pH value detection signal line 2.

The pH value sensing circuit 3 having the above-mentioned structure is used because the pH value sensing transistor T1, i.e. thin film transistor (TFT) device, has different electron mobility, on/off current ratio and threshold voltage in different acid-base environments. The present embodiment is realized by means of the linear drift characteristic of a threshold voltage Vth in environments of different pH values.

Alternatively, the pH value sensing transistor T1 is a double-gate thin film transistor. A conventional thin film transistor device has a detection accuracy of 24 mv/PH, while if the double-gate thin film transistor is used, a detection accuracy of 16 mmv/PH can be reached with a better stability. FIG. 2 shows a curve of transfer characteristics of the TFT (which reflects Vth). The horizontal ordinate represents a voltage Vgs between the gate and the source, and the longitudinal ordinate represents a drain-source saturation current Ids, and an intersection between the slope and the horizontal ordinate is Vth. A difference between the Vths is about 0.45V when the pH values are 4 and 7, respectively, so the pH value accuracy is 150 mV.

In this embodiment, the pH value sensing circuits 3 in the same row are controlled by the same drive signal line 1, and electrical signals output from the pH value sensing circuits 3 in the same column are received by the same pH value detection signal line 2. The display substrate with such a structure has simple wiring and is easy to control.

Second Embodiment

As shown in FIGS. 3-6, this embodiment provides a display substrate having a fingerprint identification function as well as the pH value detection function as described in the first embodiment, i.e. it also has a plurality of drive signal lines 1, a plurality of pH value detection signal lines 2, and a plurality of pH value sensing circuits 3 arranged on the base as described in the first embodiment. The drive signal lines 1, pH value detection signal lines 2, and pH value sensing circuits 3 in this embodiment have the same arrangement and structure as those described in the first embodiment, so they will not be described in detail any more in the following implementations.

The display substrate in this embodiment further comprises a plurality of touch signal lines 4 and a plurality of sensing signal lines 5 arranged on the base; wherein said plurality of touch signal lines 4 and said plurality of sensing signal lines 5 have crossing orthographic projections on the base to define a plurality of touch areas; a fingerprint identification circuit 6 is arranged in each of said plurality of touch areas; said fingerprint identification circuit 6 is connected to a corresponding touch signal line 4 and a corresponding sensing signal line 5 and is configured to identify fingerprints.

Figure 3:
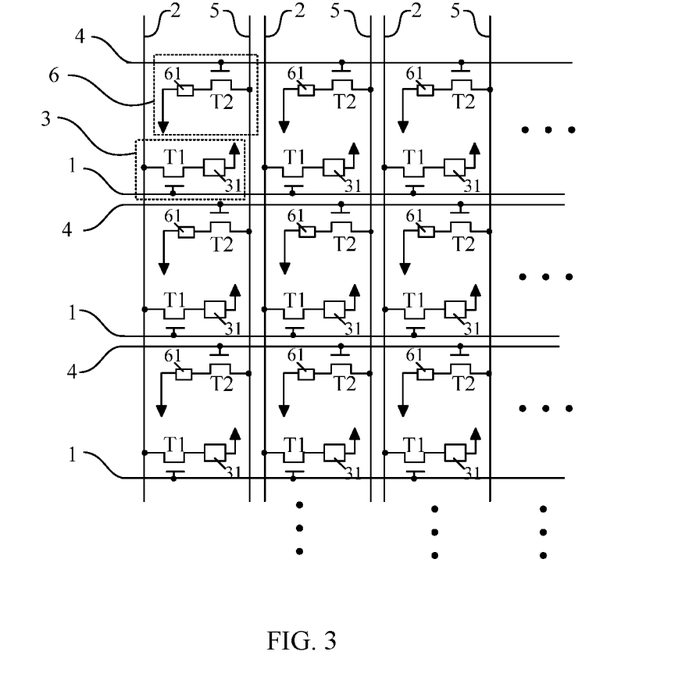
FIG. 3 is a structural diagram of a first implementation of a display substrate according to a second embodiment of the present disclosure.

As a first implementation of the present embodiment, as shown in FIG. 3, the drive signal lines 1 used for realizing the pH value detection function and the touch signal lines 4 used for realizing the fingerprint identification function are on the same side of the display substrate and are arranged alternately in parallel; meanwhile, the pH value detection signal lines 2 and the sensing signal lines 5 are also arranged alternately in parallel.

Of course, in the display substrate of the present embodiment, the part realizing the pH value detection function and the part realizing the fingerprint identification function may be in a left-right distribution pattern.

Alternatively, the drive signal lines 1 and the touch signal lines 4 can be arranged in the same layer and have the same material; the pH value detection signal lines 2 and the sensing signal lines 5 can also be arranged in the same layer and have the same material. Such an arrangement is simple in preparation and can save costs.

Figure 4:
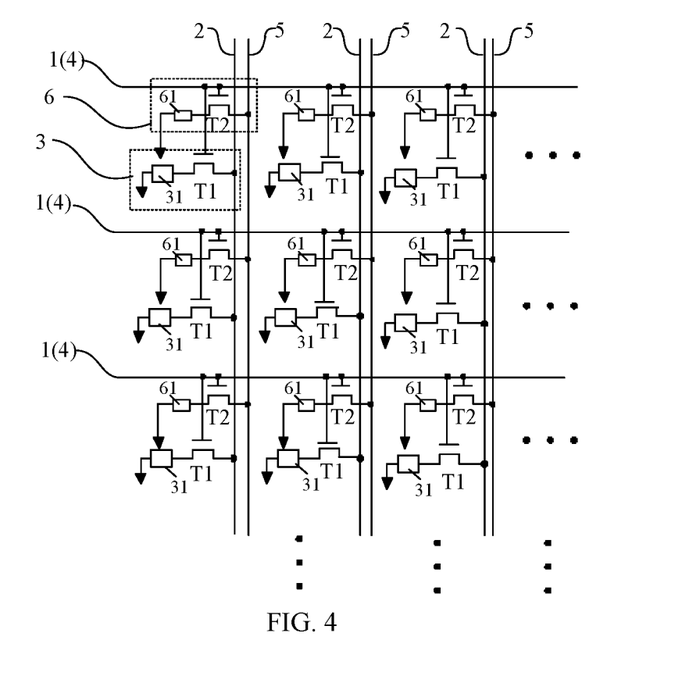
FIG. 4 is a structural diagram of a second implementation of the display substrate according to the second embodiment of the present disclosure.

As a second implementation of the present embodiment, as shown in FIG. 4, the drive signal lines 1 and the touch signal lines 4 in the display substrate are multiplexed in a time division manner. That is, the drive signal line 1 used for realizing the pH value detection function and the touch signal line 4 used for realizing the fingerprint identification function are the same signal line.

Specifically, in the fingerprint identification phase, each of the touch signal lines 4 is used for supplying a drive signal to the connected fingerprint identification circuits 6 so as to control the fingerprint identification circuits 6 to work, while the sensing signal line 5 connected to each of the fingerprint identification circuits 6 receives a feedback signal output from the each of fingerprint identification circuit 6 for determining the user's fingerprint; in the pH value detection phase, the touch signal lines 4 are multiplexed as the drive signal lines 1, and a drive signal is input into the touch signal lines row by row so as to control the pH value sensing circuits 3 to work, while the pH value detection signal line 2 connected to each of the pH value sensing circuits 3 receives a current value from the pH value sensing circuit 3 for determining the user's pH value.

Figure 5:
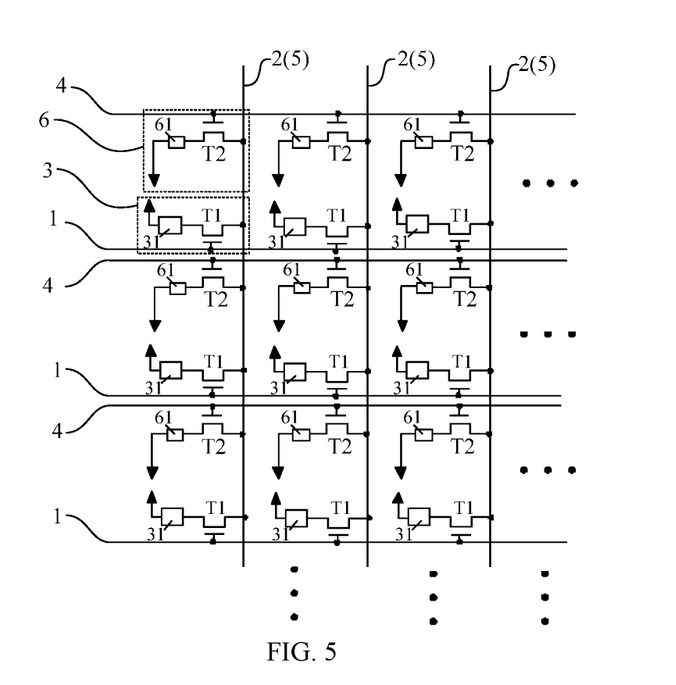
FIG. 5 is a structural diagram of a third implementation of the display substrate according to the second embodiment of the present disclosure.

As a third implementation of the present embodiment, as shown in FIG. 5, the pH value detection signal lines 2 and the sensing signal lines 5 in the display substrate are multiplexed in a time division manner. That is, the pH value detection signal line 2 used for realizing the pH value detection function and the sensing signal line 5 used for realizing the fingerprint identification function are the same signal line.

Specifically, in the fingerprint identification phase, a drive signal is input into the touch signal lines 4 row by row, and the corresponding connected fingerprint identification circuit 6 are turned on, while each of the sensing signal lines 5 receives a feedback signal from the fingerprint identification circuit 6 connected to it for determining the user's fingerprint; in the pH value detection phase, a drive signal is input into the drive signal lines 1 row by row, and the corresponding pH value sensing circuits 3 are turned on, then each of the sensing signal lines 5 is multiplexed as the pH value detection signal line 2 and receives a electrical signal output from the pH value sensing circuit 3 for determining the user's pH value.

Figure 6:
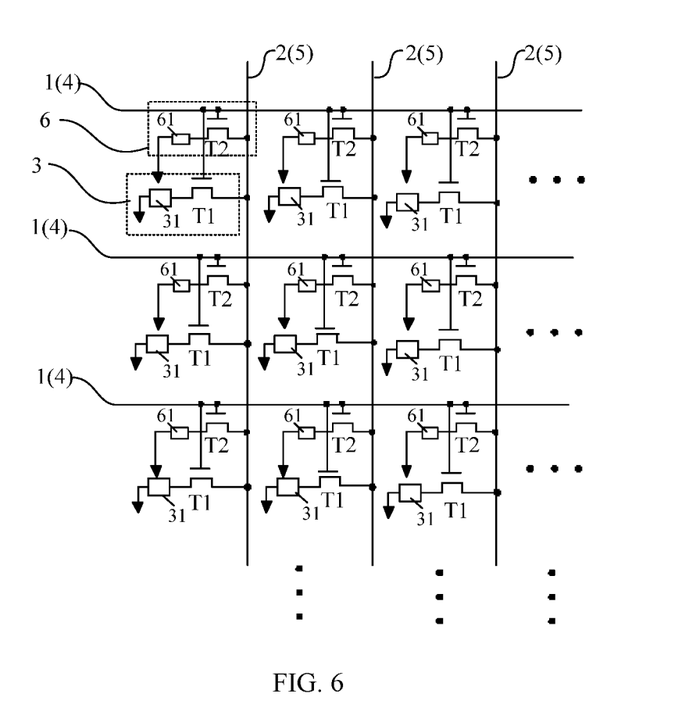
FIG. 6 is a structural diagram of a fourth implementation of the display substrate according to the second embodiment of the present disclosure.

As a fourth implementation of the present embodiment, as shown in FIG. 6, the drive signal lines 1 and the touch signal lines 4 in the display substrate are multiplexed in a time division manner. That is, the drive signal line 1 used for realizing the pH value detection function and the touch signal line 4 used for realizing the fingerprint identification function are the same signal line. The pH value detection signal lines 2 and the sensing signal lines 5 in the display substrate are multiplexed in a time division manner. That is, the pH value detection signal line 2 used for realizing the pH value detection function and the sensing signal line 5 used for realizing the fingerprint identification function are the same signal line.

Specifically, in the fingerprint identification phase, each of the touch signal lines 4 is used for supplying a drive signal to the fingerprint identification circuits 6 connected thereto so as to control the fingerprint identification circuits 6 to work, while the sensing signal line 5 connected to each of the fingerprint identification circuits 6 receives a feedback signal output from the each of fingerprint identification circuits 6 for determining the user's fingerprint; in the pH value detection phase, the touch signal lines 4 are multiplexed as the drive signal lines 1, and a drive signals is input into the touch signal lines row by row so as to control the pH value sensing circuits 3 to work, while the sensing signal lines 5 are multiplexed as the pH value detection signal lines 2 to receive electrical signals output from the pH value sensing circuits 3 for determining the user's pH value.

It can be seen that said display substrate has simple wiring and low cost.

Alternatively, in the above implementations, each of fingerprint identification circuits 6 comprises a touch transistor T2 and a photosensitive device 61. A first terminal of said touch transistor T2 is connected to a first terminal of the photosensitive device 61, and a second terminal of the photosensitive device 61 is connected to a fixed power supply terminal; and wherein control terminals of the touch transistors T2 in the same row are connected to the same touch signal line 4; and second terminals of the touch transistors T2 in the same column are connected to the same sensing signal line 5. Meanwhile, each of the pH value sensing circuits 3 comprises a pH value sensing transistor T1 and a pH value sensing electrode 31. A first terminal of said pH value sensing transistor T1 is connected to a first terminal of the pH value sensing electrode 31, and a second terminal of the pH value sensing electrode 31 is connected to a fixed power supply terminal. Control terminals of the pH value sensing transistors T1 in the same row are connected to the same drive signal line 1; and second terminals of the pH value sensing transistors T1 in the same column are connected to the same pH value detection signal line 2. In this manner, the touch transistor T2 can be prepared while preparing the pH value sensing transistor T1 so as to simplify process steps.

Alternatively, in the display substrate of the present embodiment, orthographic projections of the plurality of touch signal lines 4 and the plurality of sensing signal lines 5 on the base define a plurality of touch areas. The fingerprint identification circuit 6 is arranged in each of said plurality of touch areas, but the pH value sensing circuits 3 may be arranged in only some of the touch areas. Such an arrangement is made because as far as the display substrate is concerned, fingerprint identification requires a high precision, so the fingerprint identification circuits 6 had better be provided in each touch area, but the pH value detection does not require such a high precision, so the pH value sensing circuits 3 can be arranged only in some of the touch areas in order to save costs. Of course, it is also feasible to provide the pH value sensing circuit 3 in each of the touch areas.

Third Embodiment

Figure 7:
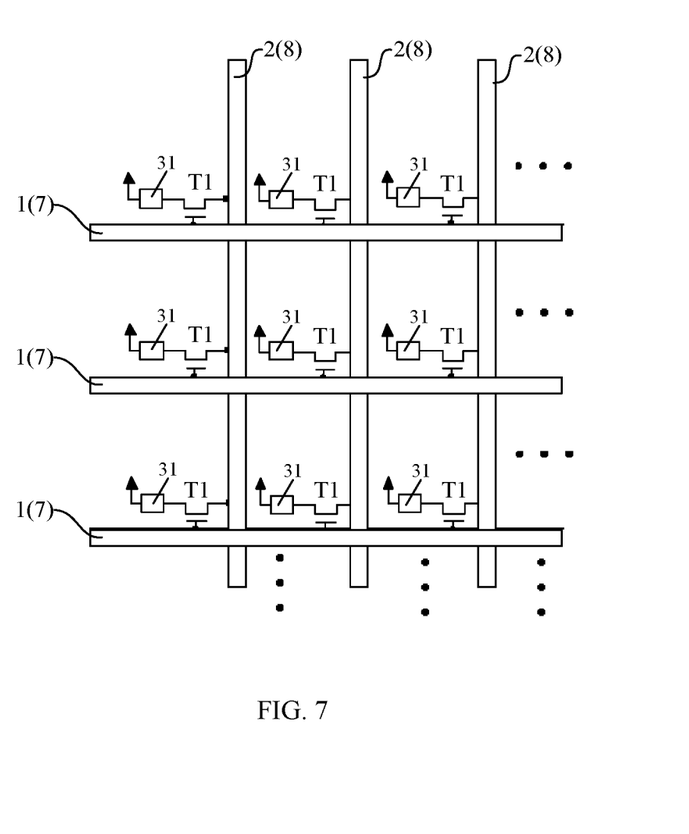
FIG. 7 is a structural diagram of a display substrate according to a third embodiment of the present disclosure.

As shown in FIG. 7, this embodiment provides a display substrate having a touch function, which comprises: a plurality of touch electrodes 7 and a plurality of sensing electrodes 8 arranged on a base; and orthographic projections of said plurality of touch electrodes 7 and said plurality of sensing electrodes 8 on the base are crossing (the touch electrodes 7 and the sensing electrodes 8 forming mutual capacitances at crossing positions). Meanwhile, said display substrate further has the pH value detection function as described in the first embodiment, i.e. it has a plurality of drive signal lines 1, a plurality of pH value detection signal lines 2, a plurality of pH value sensing circuits 3 arranged on the base as described in the first embodiment. The drive signal lines 1, pH value detection signal lines 2, and pH value sensing circuits 3 in this embodiment have the same arrangement and structure as those described in the first embodiment, so they will not be described in detail any more in the following implementations.

It can be seen that in this embodiment, the touch function and the pH value detection function are both integrated on the display substrate. Specifically, in the touch phase, a touch signal is input into the touch electrodes 7 row by row, and by detecting voltage changes on the sensing electrodes 8, positions of touch points can be determined; in the fingerprint identification phase, a drive signal is input into the drive signal lines 1 row by row, and the pH value detection signal lines 2 receive current values output by the pH value sensing circuits 3 to determine the user's pH value, thereby determining health condition of the user.

As an alternative implementation of the present embodiment, as shown in FIG. 7, each of the touch electrodes 7 is multiplexed as a drive signal line 1 in a time division manner. That is, the touch electrode 7 and the drive signal line 1 are the same signal line. Meanwhile, each of the sensing electrodes 8 is multiplexed as a pH value detection signal line 2 in a time division manner. That is, the sensing electrode 8 and the pH value detection signal line 2 are the same signal line.

Specifically, in the touch phase, a touch signal is input into the touch electrodes 7 row by row, and by detecting voltage changes on the sensing electrodes 8, positions of touch points can be determined; in the pH value detection phase, the touch electrodes 7 are multiplexed as drive signal lines 1 for providing drive signals to the pH value sensing circuits 3; the sensing electrodes 8 are multiplexed as the pH value detection signal lines 2 for receiving electrical signals output from the pH value sensing circuit 3 for determining the user's pH value.

Said display substrate has a simple structure and low manufacturing costs.

Orthographic projections of the plurality of touch electrodes 7 and the plurality of sensing electrodes 8 on the base are crossing to define a plurality of touch areas, and the pH value sensing circuits 3 are arranged in at least some of the touch areas. Alternatively, the pH value sensing circuits 3 are arranged only in some of the touch areas so as to effectively save costs. Of course, it is also feasible to arrange the pH value sensing circuits 3 in each of the touch areas.

On the basis of the present embodiment, only the touch electrodes 7 and the drive signal lines 1 are multiplexed in a time division manner, i.e. in the pH value detection phase, the touch electrodes 7 are multiplexed as the drive signal lines 1 for supplying drive signals to the pH value sensing circuits 3; or only the sensing electrodes 8 and the pH value detection signal lines 2 are multiplexed in a time division manner, i.e. in the pH value detection phase, the sensing electrodes 8 are multiplexed as the pH value detection signal lines 2 for receiving electrical signals output from the pH value sensing circuits 3.

In addition, the present disclosure further provides a display apparatus, which comprises any one of the display substrates described in the first to third embodiments. Therefore, said display apparatus has a pH value detection function.

The display apparatus can be a liquid crystal display apparatus or an electroluminescent display apparatus, or any product or component having the display function, such as a liquid crystal panel, electronic paper, an OLED panel, a mobile phone, a tablet PC, a TV, a monitor, a laptop computer, a digital photo frame, a navigator, etc.

It shall be understood that the above embodiments are merely exemplary embodiments given for illustrating the principle of the present disclosure, but the present disclosure is not limited to these embodiments. Those ordinarily skilled in the art can make various changes and improvements without departing from the spirit and substance of the present disclosure, and such changes and improvements shall also fall into the protection scope of the present disclosure.

The invention claimed is:

1. A display substrate, comprising: a base, a plurality of drive signal lines, a plurality of pH value detection signal lines, and a plurality of pH value sensing circuits arranged on the base; each of said plurality of pH value sensing circuits being connected to a corresponding drive signal line and a corresponding pH value detection signal line; wherein
    the drive signal line is configured to provide a drive signal to the pH value sensing circuits connected thereto so as to control said pH value sensing circuits to work or not;
    the pH value sensing circuit is configured to sense a pH value under a working state and output a corresponding electrical signal;
    the pH value detection signal line is configured to receive the electrical signal output by the pH value sensing circuit;
    a plurality of touch signal lines and a plurality of sensing signal lines arranged on the base; wherein said plurality of touch signal lines and said plurality of sensing signal lines have crossing orthographic projections on the base to define a plurality of touch areas; a fingerprint identification circuit is arranged in each of said plurality of touch areas; said fingerprint identification circuit is connected to a corresponding touch signal line and a corresponding sensing signal line and is configured to identify fingerprints.

2. The display substrate according to claim 1, wherein orthographic projections of said plurality of drive signal lines and said plurality of pH value detection signal lines on the base are crossing, and a pH value sensing circuit is arranged within an area defined by each crossing position.

3. The display substrate according to claim 2, wherein the pH value sensing circuit comprises a pH value sensing transistor and a pH value sensing electrode, a first terminal of said pH value sensing transistor is connected to a first terminal of the pH value sensing electrode, and a second terminal of the pH value sensing electrode is connected to a fixed power supply terminal; and wherein, control terminals of the pH value sensing transistors in the same row are connected to the same drive signal line; and second terminals of the pH value sensing transistors in the same column are connected to the same pH value detection signal line.

4. The display substrate according to claim 3, wherein said pH value sensing transistor is a double-gate thin film transistor.

5. The display substrate according to claim 1, wherein at least some of the plurality of touch areas have the pH value sensing circuits arranged therein.

6. The display substrate according to claim 1, wherein said touch signal lines and said drive signal lines are arranged in the same layer and are of the same material.

7. The display substrate according to claim 1, wherein said sensing signals lines and said pH value detection signal lines are arranged in the same layer and are of the same material.

8. The display substrate according to claim 1, wherein in a pH value detection phase, said touch signal lines are multiplexed as said drive signal lines so as to provide drive signals to said pH value sensing circuits.

9. The display substrate according to claim 1, wherein in the pH value detection phase, said sensing signal lines are multiplexed as said pH value detection signal lines so as to receive electrical signals output from said pH value sensing circuits.

10. The display substrate according to claim 1, wherein the fingerprint identification circuit comprises a touch transistor and a photosensitive device, a first terminal of said touch transistor is connected to a first terminal of said photosensitive device, and a second terminal of said photosensitive device is connected to the fixed power supply terminal; and wherein, control terminals of the touch transistors in the same row are connected to the same touch signal line; and second terminals of the touch transistors in the same column are connected to the same sensing signal line.

11. The display substrate according to claim 1, further comprising a signal processing circuit, which is connected to the pH value detection signal lines and is configured to receive and process the electrical signals received by said pH value detection signal lines so as to obtain pH values corresponding to said electrical signals.

12. A display apparatus, comprising the display substrate according to claim 1.

13. The display apparatus according to claim 12, wherein orthographic projections of said plurality of drive signal lines and said plurality of pH value detection signal lines on the base are crossing, and a pH value sensing circuit is arranged within an area defined by each crossing position.

14. The display apparatus according to claim 13, wherein the pH value sensing circuit comprises a pH value sensing transistor and a pH value sensing electrode, a first terminal of said pH value sensing transistor is connected to a first terminal of the pH value sensing electrode, and a second terminal of the pH value sensing electrode is connected to a fixed power supply terminal; and wherein, control terminals of the pH value sensing transistors in the same row are connected to the same drive signal line; and second terminals of the pH value sensing transistors in the same column are connected to the same pH value detection signal line.

15. The display apparatus according to claim 14, wherein said pH value sensing transistor is a double-gate thin film transistor.

16. A display substrate, comprising: a base, a plurality of drive signal lines, a plurality of pH value detection signal lines, and a plurality of pH value sensing circuits arranged on the base; each of said plurality of pH value sensing circuits being connected to a corresponding drive signal line and a corresponding pH value detection signal line; wherein the drive signal line is configured to provide a drive signal to the pH value sensing circuits connected thereto so as to control said pH value sensing circuits to work or not;

the pH value sensing circuit is configured to sense a pH value under a working state and output a corresponding electrical signal;

the pH value detection signal line is configured to receive the electrical signal output by the pH value sensing circuit;

a plurality of touch electrodes and a plurality of sensing electrodes arranged on the base, and wherein orthographic projections of said plurality of touch electrodes and said plurality of sensing electrodes on the base are crossing, wherein said plurality of touch electrodes and said plurality of sensing electrodes have crossing orthographic projections on the base to define a plurality of touch areas, a fingerprint identification circuit is arranged in each of said plurality of touch areas; said fingerprint identification circuit is connected to a corresponding touch electrode and a corresponding sensing electrode and is configured to identity fingerprints.

17. The display substrate according to claim 16, wherein at least some of said plurality of touch areas have the pH value sensing circuits arranged therein.

18. The display substrate according to claim 16, wherein in the pH value detection phase, said touch electrodes are multiplexed as the drive signal lines so as to provide drive signals to said pH value sensing circuits.

19. The display substrate according to claim 16, wherein in the pH value detection phase, said sensing electrodes are multiplexed as the pH value detection signal lines so as to receive electrical signals output from the pH value sensing circuits.

* * * * *